United States Patent [19]

Razzano et al.

[11] Patent Number: 5,420,221
[45] Date of Patent: May 30, 1995

[54] PROCESS FOR THE PRODUCTION OF LINEAR ORGANOSILOXANE POLYMERS BY DISPROPORTIONATION

[75] Inventors: John S. Razzano, Cohoes; Dennis P. Thompson, Clifton Park, both of N.Y.; Patricia P. Anderson, Williamstown, Mass.; Slawomir Rubinstajn, Schnectady, N.Y.

[73] Assignee: General Electric Company, Waterford, N.Y.

[21] Appl. No.: 92,450

[22] Filed: Jul. 15, 1993

[51] Int. Cl.⁶ ............................................. C08G 77/10
[52] U.S. Cl. ....................................... 528/16; 528/18; 528/21; 528/23
[58] Field of Search ........................ 528/16, 18, 21, 23

[56] References Cited

U.S. PATENT DOCUMENTS

| | | |
|---|---|---|
| 2,830,967 | 4/1958 | Nitsche et al. |
| 2,990,419 | 6/1961 | Nitzsche et al. |
| 3,186,967 | 6/1965 | Nitzsche et al. |
| 3,398,176 | 8/1968 | Nitzsche et al. |
| 3,706,775 | 12/1972 | Nitzsche et al. |
| 3,839,388 | 10/1974 | Nitzsche et al. |
| 4,426,240 | 1/1984 | Louis et al. |
| 4,725,643 | 2/1988 | Burkhardt. |
| 4,888,405 | 12/1989 | Gamon et al. |
| 4,975,510 | 12/1990 | Wegehaupt et al. |
| 5,008,229 | 4/1991 | Schuster et al. |
| 5,009,934 | 4/1991 | Wenski et al. |
| 5,206,328 | 4/1993 | Okamura et al. |
| 5,210,131 | 5/1993 | Gilson et al. |

FOREIGN PATENT DOCUMENTS

| | | |
|---|---|---|
| 0503825 | 9/1992 | European Pat. Off. |
| 2252969 | 8/1992 | United Kingdom. |
| 2252975 | 8/1992 | United Kingdom. |

*Primary Examiner*—Melvin I. Marquis

[57] ABSTRACT

A process disclosed for the production of organosiloxanes which is based on the use of a judiciously selected catalyst, e.g., a phosphorus-nitrogen homopolymeric or oligomeric compound, a derivative thereof, a complex thereof, sulfuric acid, a fluorinated alkane sulfonic acid, a kaolin clay, or a mixture of any of the foregoing, to disproportionate or to condense and disproportionate a mixture of two different organosiloxanes which have different molecular weights, without, at the same time, increasing the cyclics content of the mixture.

16 Claims, 1 Drawing Sheet

PROCESS FOR THE PRODUCTION OF LINEAR ORGANOSILOXANE POLYMERS BY DISPROPORTIONATION

The present invention relates to a novel process to produce organosiloxane polymers. More particularly, it is concerned with process conditions and catalysts for the preparation of linear organopolysiloxanes by disproportionating, or condensing and disproportionating, two organopolysiloxane starting materials having different molecular weights; the products of the disproportionation process having a molecular weight between those of the starting materials.

BACKGROUND OF THE INVENTION

Organosiloxane polymers are prepared on an industrial scale using two basic processes. The most widely practiced process is known as the equilibration process which involves the rearrangement of siloxane bonds to form an equilibrated mixture. The term equilibration is used to describe the phenomenon which exists when the ratio of linear organosiloxane polymers to cyclic organosiloxane oligomers is maintained at a constant value. When dimethyl siloxane is polymerized, equilibrium is reached when the ratio of linear polymer to cyclic oligomers is about 86:14 on a weight-weight basis. A constant ratio of linear to cyclic organosiloxanes is always reached even when the starting material is a cyclic organosiloxane, a mixture of cyclic material and linear material or an all linear monomer or oligomer.

Equilibration is reached by the use of a wide variety of acidic or basic materials as catalysts. During the equilibration process, a constant breaking and forming of siloxane bonds takes place until the equilibrium point is reached. The massive breaking and forming of siloxane bonds permits the use of chainstoppers which will react to form a terminal non-reactive group on the end of the polysiloxane molecule. The cyclic oligmers are removed from the reaction mixture at the end of the equilibration process by a stripping process after deactivation or removal of the catalyst. The formation of cyclics is a substantial drawback because it adds to the cost of the process and extends the time necessary to complete the processes.

An alternative process for producing organosiloxane polymers is condensation which promotes the head to tail condensation of siloxane monomers or oligomers. The condensation processes generally depend on the removal of water to form higher molecular weight polymers. Cyclics are not produced in the condensation process. Useful condensation catalysts include phosphorus nitrogen compounds (PNC). Relatively mild acids and bases have also been used as condensation catalysts and strong acids and bases have been used as condensation catalysts at temperatures that will not result in equilibration and the formation of cyclic organosiloxanes. The general procedure which is used in the condensation process is to combine one disilanol monomer or oligomer with an acidic, basic or PNC catalyst and after the desired polymer has reached the desired molecular weight, the polymerization is terminated. The reaction may be terminated by deactivating the catalyst using a suitable alkaline or acidic material. The neutralization will prevent further polymerization and will permit the use of the polymer without further purification.

In the prior art patents which describe condensation reactions with PNC catalysts, there was a recognition that in addition to the condensation reaction that was taking place, rearrangement of the siloxane could take place with little or no formation of cyclic siloxanes. In other prior art, there was little or no recognition that certain other known condensation catalysts of the family of acids, such as sulfuric acid, fluorinated alkanesulfonic acids, or clays, especially kaolin, function without substantial increase in cyclic contents. With respect to the PNC catalysts, in U.S. Pat. No. 2,830,967 there is described a process which is based on the use of a PNC catalyst and a liquid organosiloxane. This process is described as causing the organosiloxane polymers to "condense and rearrange" and it is disclosed that the catalyst may be left in the final product because it has no "depolymerizing effect". The examples and text of U.S. Pat. No. 2,830,967 all disclose the use of a single siloxane which is polymerized to form a product having a higher molecular weight. GB 2 252 975A discloses a method of making organosiloxanes using a complexed PNC catalyst of the formula $[X(PNX_2=N)_nPX_3]+B$ where X is a halide atom and B is a complexing agent comprising an anion of a Lewis acid. This patent states that traces of catalyst may re-equilibrate an organopolysiloxane to produce cyclics and for this reason the traces of the catalyst should be neutralized.

U.S. Pat. No. 5,008,229 discloses a process for the condensation of one organosiloxane having silicon bonded hydroxyl groups or a mixture of organosiloxanes having silicon bonded hydroxyl groups in the presence of a PNC catalyst and a solubilizer. The text of U.S. Pat. No. 5,008,229 points out that the condensation process is always carried out under reduced pressure, and this will be expected to lead to high molecular weight products, such as gums instead of disproportionated products.

U.S. Pat. No. 5,009,934 discloses the reaction of a high molecular weight dihydroxydimethylpolysiloxane and 1,3-dihydrogentetramethyldisiloxane in the presence of PNC to produce a complex mixture of hydride-terminated polysiloxanes. This procedure requires that at least one of the organosiloxanes must be hydrogen terminated and the product is also hydrogen terminated.

The applicants have discovered that if two or more different organosiloxanes, which have different molecular weights, are combined at weight ratios of from about 1:99 to 99:1 or more preferably from 5:95 to 95:5 in the presence of a judiciously selected condensation/disproportionation catalyst, as will be described later, e.g., acids, some types of kaolin, a PNC-, or oligomerized PNC catalyst, a complexed PNC catalyst, an acid derivative of a PNC catalyst, mixtures of any of them, and the like, a reaction will take place which will result in the formation of a different organosiloxane which has a molecular weight lower than the molecular weight of the organosiloxane reactant which has the highest molecular weight of one of the two starting organosiloxanes. In a two-step modification of the process, one of the reactants is first made by condensing a high silanol content polydiorganosiloxane, followed by disproportionation of the mixture, as described. In any event, the reaction does not result in the formation of any significant quantities of cyclic siloxanes, i.e. less than 6 wt %, preferably below 2 wt %, and the products may be directly utilized for the formulation of commercial products without any substantial purification provided that any residual catalyst is neutralized.

The novel process of the invention is being characterized as a disproportionation reaction to point out that the product is a lower molecular weight product than one of the two starting materials. It is believed that the process of the invention depends upon the breaking and reforming of siloxane bonds but the applicants do not wish to be bound to any theory which may explain the results provided by the process of the invention.

It is therefore a primary object of the invention to provide a process for the preparation of organosiloxanes which does not result in the formation of any significant quantity of cyclic siloxanes.

It is also an object of the present invention to provide a process for the preparation of low viscosity organopolysiloxane fluids without the formation of any significant quantity of cyclic organopolysiloxanes.

It is also an object of the present invention to provide a process for the rapid preparation of a low viscosity polyorganosiloxane fluid with a normal molecular weight distribution by the disproportionation of two or more reactants having different molecular weights.

It is also an object of the present invention to provide a process for the preparation of a organosiloxane copolymer having silicon hydride group and silicon vinyl groups.

It is a further object to start with a low molecular weight, high silanol content siloxane material and produce low molecular weight triorganosiloxy terminated oils.

These and other objects of the invention will become apparent from the present specification.

SUMMARY OF THE INVENTION

The invention comprises a process for producing an organosiloxane of the formula:

Formula I wherein $R^1$ is selected from the group consisting of saturated, unsaturated or aryl hydrocarbons having from 1 to 8 carbon atoms; or halogenated hydrocarbons having from 1 to 8 carbon atoms; $R^2$ may be the same as $R^1$ or can be $R^1$ group attached to an oxygen atom; $R^3$ may be the same as $R^1$ or may be hydrogen or OH; n may be 1 to 5000; and the ratio of the sum of $R^1+R^2+R^3$ to silicon atoms in the final product is from 1.9 to 2.1, said process comprising disproportionating a mixture of a siloxane of the formula:

Formula II

,R and R are the same as herein above defined and r has a value of 500 to 15,000; and a siloxane of the formula:

Formula III wherein $R^1$, $R^2$ and $R^3$ are the same as herein above defined and s has a value of 0 to 300, with the proviso that the total amount of silanol in Formula II and III may not exceed about 1,000 ppm by weight; in the presence of an effective disproportionating amount of a catalyst which comprises a compound which is capable of disproportionating the mixture of an organosiloxane of Formula II and Formula III without substantially increasing the cyclics content of the mixture; and thereafter recovering an organosiloxane of Formula I.

Also contemplated by the invention is a two-step process for producing an organosiloxane of the formula:

Formula I wherein $R^1$ is selected from the group consisting of saturated, unsaturated or aryl hydrocarbons having from 1 to 8 carbon atoms; or halogenated hydrocarbons having from 1 to 8 carbon atoms; $R^2$ may be the same as $R^1$ or can be $R^1$ group attached to an oxygen atom; $R^3$ may be the same as $R^1$ or may be hydrogen or OH; n may be 1 to 5000;
and the ratio of the sum of $R^1+R^2+R^3$ to silicon atoms in the final product is from 1.9 to 2.1, said process comprising, as a first step

(I) providing a starting material of Formula IIa

Formula IIa wherein $R^1$, $R^2$ and $R^3$ are the same as hereinabove defined and r has a value of 500 to 15,000 by condensing a corresponding disilanol terminated organosiloxane having a Si—OH content above 1000 ppm wherein r' has a value of from 10 to 15,000 by means of a condensation catalyst, such as a PNC compound or sodium hydroxide, and the like, until the Si—OH content is reduced to below about 1000 ppm, and, thereafter, as a second step, (II) disproportionating a mixture of the condensed siloxane produced in step (I) of the formula:

Formula II wherein $R^1$, $R^2$ and $R^3$ are the same as herein above defined and r has a value of 500 to 15,000; and a siloxane of the formula:

Formula III wherein $R^1$, $R^2$ and $R^3$ are the same as herein above defined and s has a value of 0 to 300, with the proviso that the total amount of silanol in Formula I and II may not exceed about 1,000 ppm by weight; in the presence of an effective disproportionating amount of a catalyst which comprises a compound which is capable of disproportionating said mixture of an organosiloxane of Formula II and Formula III without substantially increasing the cyclics content of said mixture; and thereafter recovering an organosiloxane of Formula I. This two-step process allows the product of the process to have a monomodal distribution.

In preferred features, the invention contemplates processes as defined above, wherein the catalyst compound has the ability to effect the conversion of a mixture of polyorganosiloxane of Formula II and the polyorganosiloxane of Formula III to a disproportionated product of Formula I, at a temperature of about 90° C., within a relatively short time, in the range of from about 30 to about 90 minutes, without, at the same time, substantially increasing the content of cyclic by-products. Such a test aids in the selection of useful catalysts for practicing the invention. Numerous experiments using such a test have demonstrated that the following otherwise catalytically-active substances will not work, either because of significant cyclics formation, or a complete lack of rearrangement activity, and the like: hydrochloric acid, hydrobromic acid, acid-treated clay (Filtrol®), phosphoric acid. $H^+$ $FeCl_4^-$, methane sulfonic acid, potassium hydroxide, sulfonic acid ion exchange resins, etc.

In any event, special mention is made of processes of the present invention carried out with a catalytic compound selected from a phosphorus-nitrogen homopolymeric or oligomeric compound, a derivative thereof, a complex thereof, sulfuric acid, a fluorinated alkane sulfonic acid, selected grades of kaolin clay, or a mixture of any of the foregoing.

DETAILED DESCRIPTION OF THE INVENTION

The present invention provides an efficient method for the disproportionation and condensation and disproportionation of a mixtures of a high and a low viscosity organosiloxane. In a preferred embodiment of the invention, organosiloxanes of Formula I may be prepared using a blend of organosiloxanes of Formula II and Formula III. When r in Formula II is 5,000 and s in Formula III is 1, the process of the invention will produce an organosiloxane of Formula I where n is greater than 2 with a final value being a function of the amount of chain terminating species contained in the original blend. If it is desired to produce an organosiloxane wherein n is equal to 20, a blend of an organosiloxane where r in Formula II equals 500 and an organosiloxane where s in Formula III equals 0–5 could be disproportionated to form the desired product. In the alternative, an organosiloxane of Formula I may be prepared with n having a value of from 0 to 5,000 by blending an organosiloxane of Formula II wherein r is 0, with an organosiloxane of Formula III where s is equal to 5000 and disproportionating the blend using the process of the invention to form the desired organosiloxane without the formation of any substantial amount of cyclic organosiloxanes.

In the practice of the process of the present invention it is important that the silanol content of the blended organosiloxanes be very low since the presence of high levels of silanol (or water formed from the silanols) will dramatically reduce the rate of disproportionation of the blends of organosiloxanes and/or may prevent the blend from reaching the ultimate theoretical viscosity potential of the product blend. The general upper limit for silanol content is about 3,000, preferably 1,000, most preferably 750, ppm based on the total weight of the organosiloxanes in the blend. Higher amounts of catalyst are needed at higher silanol contents in order to most efficiently utilize the Formula III compounds.

As has been mentioned, it is possible to start with a blend, one a high silanol content organopolysiloxane, and to precondense in a first step, then add a second quantity of catalyst, and thereby obtain an equilibrium viscosity very quickly; this is contemplated to be a preferred feature of the invention.

If one of the organosiloxanes of Formula II or III is a high molecular weight organosiloxane containing 50–500 ppm silanol as chain terminator units, such a material may be used in the process of the invention. High silanol oils containing 1 to 8 wt % silanol can be employed as long as the total silanol content of the blend remains low. For example, if the major components of an organosiloxane blend contain no silanol, then 1% by weight of the blend could be a silanol organosiloxane containing 5 wt % silanol groups because this would give a total silanol content in the blend of 50 ppm by weight. The reaction may be carried out at a temperature of from 20° to 180° C. and more preferably at 50° to 140° C. Generally the reaction is carried out at atmospheric pressure but if desired a pressure of 1 torr to 1000 torr may be employed.

The process of the invention may be carried out without the addition of any solvent provided that the reactants are miscible with the catalyst. The length of time required for the disproportionation reaction will vary from a few minutes to up to 16 hours depending on the nature of the materials and the amount of the catalyst which is employed.

Among the most preferred catalysts for use in the practice of the invention are included phosphorus-nitrogen compounds which have been utilized in the prior art as condensation catalysts for making high molecular disilanols. Some of these catalysts are described in U.S. Pat. Nos. 2,830,967; 3,186,967; 3,398,967; 3,839,388; 2,990,419; 3,706,775; 4,725,643; 4,975,510; 4,888,405 and 5,008,229; U.K. 2 252 975A; U.K. 2 252 969A; and EPA 0 503 825A1 all of which are incorporated by reference. Illustrative, but not limitative of such useful phosphorus-nitrogen catalysts include $Cl_3PN(PNCl_2)_xPCl_3\cdot PCl_6(x=1)$ and short-chain linear phosphazenes of Formulae (Ia) or I(b):

(Ia)

(Ib)

where n=0 or an integer from 1 to 8; m=0 or an integer of 1; p=0 or an integer of 1; q=0 or an integer of from 1 to 2; X=halogen; Y=OH, OR, O(O)CR, wherein R is alkyl or aryl, as catalysts for polycondensation and redistribution of organopolysiloxanes.

Also contemplated are reaction products of the linear PNC compounds with compounds containing active protons with pKa values below 18, such as carboxylic acids, halogenoalkane carboxylic acids, sulfonic acids, alcohols, phenols and water.

Preferred species of the new catalysts have a low content of chlorine and comprise those of the Formulae (Ic), (Id) and I(e):

(Ic)

(Id)

(Ie)

where n is 0 or an integer of from 1 to 8, preferably from 1 to 3. Compounds of Formula (Ie) wherein n is 0 or 1 are soluble in halogen-free solvents, such as ethers, ketones, e.g., acetone, esters, e.g., ethyl acetate, aromatic hydrocarbons, e.g., toluene, mixtures of any of them, and the like.

Among the preferred embodiments are short-chain linear phosphazene catalysts (Ia), (Ib), (Ic), (Id) and (Ie) wherein each X group denotes a chlorine atom; those wherein each Y group denotes a hydroxyl group; those wherein m values can vary from 0 to 1; those wherein q values can vary from 0 to 2; those wherein p values can vary from 0 to 1.

The amount of the catalyst that is employed is an effective amount to readily disproportionate the starting materials. The amount to be employed is not critical and may vary from 5 to 500 parts per million and more preferably from 10 to 100 parts per million of total weight of the organosiloxane starting materials used in the practice of the invention. Higher amounts of catalyst will be used with higher silanol contents in the starting materials, e.g., 1000 to 3000 ppm of silanol. The catalyst is preferably dispersed or dissolved in an inert solvent at a concentration of from 0.1 to 10 weight percent and preferably 0.5 to 5 weight percent in order to facilitate the handling of the catalyst and to facilitate dispersing the catalyst in the reaction mixture. Suitable solvents for the catalyst include esters, such as aliphatic esters, ethers, such as aliphatic ethers, aromatics, such as toluene, benzene, liquid siloxanes, chlorinated aliphatic and aromatic organic solvents such as methylene chloride, trichloroethane, 1,3,5-trichlorobenzene and the like.

After the disproportionation reaction has proceeded to the point where the desired product has been formed, the reaction may be terminated by raising the temperature to from 150° to 250° C. or more preferably to a temperature of from 180° to 220° C. In the alternative, the catalyst may be inactivated by neutralization with an alkaline material. Suitable alkaline materials include ammonia, inorganic alkaline compounds such as lithium hydroxide, sodium hydroxide, calcium oxide, calcium hydroxide, magnesium oxide, sodium carbonate, sodium bicarbonate and the like; hexamethyldisilazane, aliphatic primary, secondary and tertiary organic amines such as ethyl amine, diethyl amine, triethyl amine, propyl amine and the like. The amount of the neutralizing agent which is used should be sufficient to terminate the further disproportionation of the organosiloxanes in the reaction mixture and provide a stable product. This amount may be determined by reference to the total acid content and will generally be from 10 to 100 ppm of neutralizing agent based on the total weight of the reactants.

The procedures for the recovery of the reaction products are conventional and are not a part of the present invention.

In one embodiment of the invention, a low molecular weight disilanol may be condensed to form a high molecular weight disilanol in order to prepare a starting material for the present invention. This condensation will result in a material which has a sufficiently low Si—OH content (e.g., less than 750 or 1000 ppm) which will make the disilanol useful as a starting material for disproportionation and allow a monomodal distribution of the product of Formula I. In this embodiment, the condensation is carried out using an effective PNC compound and when the Si—OH content has been sufficiently reduced by the condensation reaction, a organosiloxane of Formula III and a second increment of the PNC catalyst are added to the same reactor to effect the disproportionation reaction. An M-stopped silicone oil in small amounts (e.g., 2000 ppm of M-equivalent basis) can be added during the condensation stage to keep the viscosity in a managebly useful range. After disproportionation, the reaction may be terminated using the procedures set forth above.

A wide variety of silicone polymers can be made by the process of the present invention. Fully methylated siloxane oils can be produced and such products are useful as silicone emulsions for fabric treatment, antifoams and high temperature heat transfer fluids. Very high viscosity silicones can also be made by the process of the invention and these polymers are primarily useful for the production of silicone rubber and as additives in personal care products, particularly hair treatment products. Further, vinyl-containing silicone polymers and hydride-containing polymers can be made by the process of the invention and such materials can be used in "two part addition cure RTV" products which may be used as electronic encapsulating materials, as liquid injection molding rubber for a variety of silicone products, including baby bottle nipples, computer keyboards, and the like. In addition, the instant process is particularly useful for producing siloxane copolymers which are difficult to produce by standard silicone polymerization techniques. For example, it is difficult to conventionally copolymerize polymers containing silicon-vinyl and silicon-hydride groups or silicon-phenyl and silicon-hydride groups. These problems are well known in the art and have been described in the literature. In the prior art these materials have been produced by hydrolysis of the corresponding chlorosilanes. The hydrolysis process has the undesirable characteristics of limiting molecular weight, creating a high cyclic content and generating byproduct hydrochloric acid which causes disposal problems. Using the present invention, copolymers containing silicon-vinyl and silicon-hydride units can easily be produced by disproportionation without unreasonable limits on molecular weights and without the formation of significant amounts of cyclics and without the formation of hydrochloric acid. Silicone polymers containing both vinyl and hydride may also be used in the manufacture of silicone release coatings.

DESCRIPTION OF THE PREFERRED EMBODIMENTS

The following examples are included to illustrate the invention. All viscosities were measured at 25° C. Unless otherwise indicated, all parts are by weight.

EXAMPLE 1

An organosiloxane blend was prepared by combining 1000 parts by weight of a 10000 cps polydimethylsiloxane which was terminated with trimethylsilyl groups and 40 parts of hexamethyldisiloxane. Four hundred grams of this blend were added to a wide mouth jar and 50 ppm of PNC catalyst of the type $Cl_3PN(PNCl_2)_xPCl_3 \cdot PCl_6$ (x=1), was added as a 3% solution in methylene chloride. The jar contents were vacuum deaired. Following this, spindles from a Brookfield RVF viscometer were placed in the jar and connected to the viscometer. The viscosity of the blend was continuously measured versus time in a room controlled at 25° C. and 50% relative humidity. The viscosity of the blend began to decrease quickly and was measured over a 240 minute period. The test data are set forth in Table A, col.1. The test results show that phosphonitrilic chloride is a very effective catalyst for the disproportionation of organosiloxanes.

COMPARATIVE EXAMPLE A

A total of 0.02 g of the catalyst Example 1 was added to 10 g of a mixture which contained 9.6 grams of a disiloxanol oil containing 2.1% silanol having a viscosity of 87 cps and 0.4 grams of hexamethyldisiloxane, at room temperature. The PNC catalyst began to condense the silanol and the solution turned cloudy as the water that was formed by the condensation of the silanols precipitated from solution. The silanols and/or the formed water reacts with the most labile chlorines of the catalyst and hydrolyzes part of the catalyst. After the catalyst solution stands at room temperature for 2 hours, it is placed in a vacuum oven at 134° C. and 18 mm Hg pressure for 2 minutes. This procedure removes the water from the hydrolyzed catalyst along with most of the free hydrochloric acid formed by the hydrolysis. The hydrolyzed catalyst solution is added to the 390 grams of a siloxane blend which is identical to the blend used as the starting material for Example 1. The mixture which is formed has the same final composition as the blend-catalyst mixture at the start of the procedure described in Example 1. This mixture in then deaired and the changes in viscosity were monitored using the same procedure that was used in Example 1. The test data are described in Table A, col. 2. It is readily apparent that when the phosphonitrilic catalyst is contacted with a high silanol containing oil the ability of the phosphonitrilic chloride catalyst to function as a disproportionation catalyst is dramatically less effective. For this reason, viscosity measurements were only taken for 45 minutes.

EXAMPLE 2

To further demonstrate that an unmodified phosphonitrilic chloride is a very active disproportionation catalyst, 50 ppm of the phosphonitrilic chloride catalyst of Example 1 were added to the composition of Comparative Example A at the 45 minute point. The additional catalyst was quickly mixed in, deaired and the viscosity was measured using the same procedure that was employed in Example 1. The test data are reported in Table A, col. 3. The addition of catalyst caused a quick and dramatic viscosity decrease which clearly shows the high disproportionation activity of the unmodified catalyst.

TABLE A

| (Column) Total Time (minutes) | Viscosity (cps) | | |
|---|---|---|---|
| | 1 | 2 | 3 |
| 0 (before Cat. Addition) | 6400 | 6400 | |
| 4 | 1040 | 5400 | |
| 6 | 820 | 5000 | |
| 10 | 460 | 4500 | |
| 15 | 320 | 4180 | |
| 20 | 260 | 4600 | |
| 30 | 204 | 3700 | |
| 45(1) | 163 | 2860 | |
| 55 | 150 | | 1450(2) |
| 65 | 142 | | 250 |
| 75 | 136 | | 185 |
| 100 | 125 | | 135 |
| 240 | 105 | | 105 |

1. A second increment of catalyst was added at this point.
2. 50 ppm of the unmodified phosphonitrilic chloride catalyst of Example 1 was added at this time.

EXAMPLE 3

This example demonstrates the advantage of a progress where a polydimethyldisiloxanediol of greater than 750 ppm Si—OH content is precondensed with an PNC catalyst and the precondensed polymer subsequently disproportionated with MM and a second portion of catalyst. This results in a fluid of appropriate viscosity with a monomodal molecular weight distribution. On the other hand, when using hexamethyldisiloxane, an equivalent amount of PNC catalyst and a polydimethylsiloxanediol of greater than 750 ppm Si—OH content (without precondensation), for comparison purposes, there is incomplete chain stopper incorporation and this results in higher fluid viscosities and bimodal molecular weight distributions. This latter effect can, however, be overcome by adding greater amounts of catalyst. However, very high levels of catalyst (>100 ppm) are not generally preferred because they affect final product performance by leaving high levels of residual salts.

Example 3(a)

A 500 ml, three-necked round bottomed flask equipped with a mechanical stirrer and a vacuum inlet was charged with 117.1 g of a 110 cps silanol-endcapped polysiloxane fluid (approximately 1.4% Si—OH). The flask was placed in an oil bath which was heated to 90° C. A solution of the catalyst of Example 1 in methylene chloride (2.3% by wt, 56 microliters, 15 ppm) was added by a syringe with stirring and the flask was placed under vacuum (7 torr) to remove water formed by the silanol condensation. After about 5 minutes, the siloxane fluid was converted to a gum (weight average mol. wt. by GPC 391,000) and the silanol content was determined to be less than 100 ppm silanol. The flask contents were brought to atmospheric pressure. The vacuum inlet was replaced with a condenser. A mixture of hexamethyldisiloxane (8.6g, 7% by wt) and catalyst solution (2.3% by weight, 56 microliters, 15 ppm of the catalyst of Example 1) was added to the gum with stirring. After 15 minutes, the reaction viscosity was 38 cps with a monomodal molecular weight distribution by gas phase chromatography (GPC).

Example 3(b)

A 500 ml, three necked, round bottomed flask equipped with a mechanical stirrer and a vacuum inlet was charged with 59 g of a 64 cps silanol-stopped fluid (approximately 1.4% by weight Si—OH, 6.3% by weight volatiles at 150° C. for 1 hour) The flask was placed in an oil bath and the contents heated to 140° C. Catalyst (30 microliters as a 2.3% by wt solution of the catalyst of Example 1 in methylene chloride, 15 ppm) was added by a syringe with stirring and the flask was placed under vacuum (7 torr) to remove water formed by the silanol condensation. After three minutes, the fluid had been converted to a gum (weight average mol. wt. by GPC 470,900). The vacuum was removed and the vacuum inlet was replaced with a condenser. Hexamethyldisiloxane (4.1 g, 6.5% by wt) was added to the gum with stirring. After 15 minutes, the reaction mixture viscosity was 38 cps with a monomodal molecular weight distribution by GPC; 6.1% volatiles at 150° C. for 1 hour (volatiles consist of both cyclics and low molecular weight linear siloxanes); and approximately 50 ppm silanol.

Comparative Example 3(c)

A 500 ml, three necked flask equipped with a condenser and a mechanical stirrer was charged with 135 g of a disilanol oil (approximately 3000 cps and 1000 ppm Si—OH) and 10.16 g of hexamethyldisiloxane (7% by wt). The flask was placed in an oil bath and the contents heated to 90° C. A solution of the catalyst used in Example 1 (130 microliters which is equivalent to 30 ppm catalyst) was added via syringe, with stirring. After 30 minutes, the reaction mixture viscosity was 56 cps at 25° with a bimodal molecular weight distribution.

Comparative Example 3(d)

In a similar manner a 1 to 1 mixture (74 g each) of a 3000 cps disilanol oil (approximately 1000 ppm Si—OH) and a 110 cps silanol stopped fluid (approximately 1.4% Si—OH) which gave a content of about 7500 ppm of silanol in the mixture was reacted with hexamethyldisiloxane (10.95 g, 7% by wt) and 30 ppm of the catalyst of Example 1 (141 microliters of a 2.3% by wt solution in methylene chloride) at 90° C. After 30 minutes, the reaction mixture viscosity was 74 cps with a bimodal molecular weight distribution.

Comparative Example 3(e)

A 2:1 mixture (76 g to 38 g) of 110 cps disiloxanol stopped fluid (about 1.0% Si—OH) to 3000 cps disiloxane oil was reacted with hexamethyldisiloxane (8.58 g, 7% by weight) and the catalyst of Example 1 (30 ppm, 110 microliters of a 2.3% by weight solution in methylene chloride) at 90° C. After 30 minutes, the reaction mixture viscosity was 88 cps with a bimodal molecular weight distribution.

Comparative Example 3(f)

A silanol stopped fluid (57.4 g, 64 cps, approximately 1.4% Si—OH) was reacted with 4.0 g of hexamethyldisiloxane(7% by wt) and the catalyst of Example 1 (56 microliters of a 2.3 wt % solution in methylene chloride equivalent to 30 ppm of catalyst) at 140° C. After 60 minutes the reaction mixture viscosity was 198 cps with a bimodal molecular weight distribution. If the catalyst content is increased to 100 ppm, the viscosity is expected to increase to greater than 60, but less than 100.

PROCEDURE A

Preparation of $OCl_2PNPCl_3$

A 100 ml flask was charged with 20.8 g (0.1 mol) of phosphorus pentachloride, 2.93 g of ammonium sulfate and 50 ml of symtetrachloroethane. The mixture was stirred and refluxed over 1 hour. After the reaction was over, the solvent was removed and the product was purified by vacuum distillation (b.p. 110°–115° C./0.1 mm Hg). The yield of the title product as light yellow crystals was 12 g.

PROCEDURE B

Preparation of $OCl_2PNPCl_2NPCl_3$

A 100 ml flask was charged with 13.5 g (0.05 mol) of the title compound of Procedure A, 11.6 ml (0.055 mol) of $HN(Si(CH_3)_3)_2$ and 20 ml of methylene chloride. The mixture was stirred and refluxed over 12 hours. After the reaction was over, 10.3 g (0.05 mol) of $PCl_5$ was added, and the reaction mixture was refluxed for an additional 12 hrs. The solvent was removed by rotavaporation and product was purified by vacuum distillation (b.p. 170°–175° C./0.1 mm Hg). The yield of the title product as light yellow liquid was 8g.

PROCEDURE C

Preparation of $OCl_2PNPCl_2NPCl_2OH$ by Hydrolysis of the Product of Procedure B A 100 ml flask was charged with 0.5 g (0.0013 mol) of the product of Procedure B, and 5 ml of methylene chloride. Water (23.3 microliters, 0.0013 mol) was added. The mixture was stirred over 2 hours. After the reaction was over, solvent was removed by rotavaporation. The yield of the named product as a yellow liquid was 0.36 g.

EXAMPLE 4

A 250 ml flask equipped with mechanical stirrer, condenser and vacuum outlet was charged with 10 g of MW=80,000 polydimethylsiloxane and 2 g of hexamethyldisiloxane. The flask was heated to 90° C. After reaching the desired temperature, 18 ppm (30 microliters of 3% solution in methylene chloride) of the catalyst of Procedure C was added. Very fast lost of viscosity was observed. After 20 minutes the reaction was stopped by quenching the catalyst with hexamethyldisilazane. The resulting trimethyl-terminated silicone oil had a molecular weight MW=1000 and did not contain significant amount of oligomeric cyclic species.

EXAMPLE 5

A 250 ml flask equipped with mechanical stirrer, condenser and vacuum outlet was charged with 50 g of PS 343 (MW=26,000 polydimethylsiloxanediol, Hüls) and 7.0 g of dodecamethyltetrasiloxane as a chain stopper. Mixer was heated to 90° C. After reaching the desired temperature 18 ppm (30 microliters of 3% solution in methylene chloride) of a catalyst was added which was prepared as follows:

A 50 ml flask was charged with 4.0 g of PS 341 (MW=4,000 polydimethylsiloxanediol Hüls) organosiloxanediol and 0.8 g of nonamethyltetrasiloxane-1-ol and 10 ml of methylene chloride. Then 1 g of PNC (of Example 1) in 10 ml of methylene chloride was added at once at room temperature. After a few seconds a large amount of water was formed. The resulting turbid two phase mixture was stirred for 15 minutes. The solvents and organosilicone materials were removed from the system by heating to 80° C. under reduced pressure (0.05 mm Hg) for 2 hours to afford 0.7 g of light yellow catalytically-active viscous oil, which was dissolved in 23 ml of methylene chloride.

A very fast disproportionation was observed (considerable foam was formed and water was condensed in vacuum trap). After 30 minutes of reaction, the reaction was stopped by quenching the catalyst with hexamethyldisilazane. The resulting trimethyl-terminated silicone oil had a molecular weight, MW=3000 and did not contain any oligomeric cyclic species.

EXAMPLE 6

This example shows the preparation of a polymer which contains vinyl and hydride groups in the same polymer.

Two hundred and fifty grams of a polydimethylsiloxane having a viscosity of 10,000 cps was mixed with 50 grams of a 67 cps trimethyl-terminated silicone oil containing only methyl hydrogen siloxanes and 50 g of a 250,000 cps oil which is trimethylsiloxane-terminated and contains 13 mol% methylvinylsiloxane and 87 mol % dimethylsiloxane. The viscosity of the mixture was 22,800 cps. The mixture was heated to 90° C. and 30 ppm of the catalyst of Example 1 was added as a methylene chloride solution. The mixture was stirred for several hours and the batch cooled. The final viscosity of the disproportionated product was 700 cps, the approximately correct viscosity for the total amount of M and D groups in the product. The starting mixture had a broad molecular weight distribution resulting from a blend of materials of significantly different viscosity. The final product had a monomodal distribution with a polydispersity index of 1.75, a normal value for a fully disproportionated siloxane polymer.

EXAMPLE 7

A 3-necked, 100 ml round-bottom flask equipped with a mechanical stirrer and vacuum inlet was charged with 46 g of a 110 cps silanol-stopped fluid and 1.1 g of a 50 cps M-stopped fluid (providing about 0.2% eq. wt. of hexamethyldisiloxane). The flask was placed in an oil bath and the contents heated to 90° C. A solution of the phosphonitrilic chloride of Example 1 (2.3% by wt in methylene chloride; 23 microliters, 15 ppm PNC) was added, via syringe, with stirring. After catalyst addition, the reaction mixture was stirred at 90° C. under vacuum (approx. 7 torr) for 3 minutes, becoming a heavy oil. The flask was returned to atmospheric pressure and hexamethyldisiloxane (0.248 g, 325 microliters, 0.5 wt % MM- bringing a total equivalent MM concentration in the reaction mixture to 0.72%) and a second increment of catalyst solution (23 microliters, 15 ppm PNC) was added via a syringe with stirring. After 30 minutes the reaction mixture viscosity was 1006 cps with an increase of volatiles of about 2%.

EXAMPLE 8

A 3 necked, 100 ml round-bottom flask equipped with a mechanical stirrer and vacuum inlet was charged with 61.7 g of a 110 cps silanol stopped fluid and 0.30 g of an $MD_xM$ fluid with 41.5% equivalent M (providing about 0.2% equivalent weight of hexamethyldisiloxane). The flask was placed in an oil bath and the contents heated to 90° C. Phosphonitrilic chloride solution (2.3% wt PNC in methylene chloride; 30 microliters; 15 ppm PNC) was added, via syringe, with stirring. After catalyst addition, the reaction mixture was stirred at 90° C. for two minutes and then slowly taken to a vacuum of 45 mm Hg for 15 minutes, becoming a heavy oil. The vacuum was removed and hexamethyldisiloxane (0.475 g, 621 microliters, 0.8 wt % for a total equivalent MM content of 1.0 wt % in the reaction mixture) and PNC solution (30 microliters, 15 ppm PNC were added via syringe with stirring. After 30 minutes the viscosity of the reaction mixture was 683 cps with a volatiles content of 2.6%.

EXAMPLE 9

(a) Preparation of linear phoshonitrilic chlorides

A 100 ml flask was charged with 12.5 g of phosphorus pentachloride, 2.14 g of ammonium chloride, 6.0 g of antimony pentachloride and 30 ml of 1, 1, 2, 2-tetrachloroethane. The mixture was stirred and refluxed over 8 hours. After the reaction was over, the solution was filtered to remove solid compounds. The tetrachloroethane was removed under vacuum. A catalyst of the formula $PCl_3(NPCl_2)_nNPCl_3 \cdot SbCl_6$ (n=1,2) was obtained as a yellow solid which is soluble in methylene chloride.

(b) Redistribution of high molecular weight polysiloxanes with decamethylhyltetrasiloxane in the presence of $PCl_3(NPCl_2)_nNPCl_3 \cdot SbCl_6$ A 250 ml flask equipped with a mechanical stirrer, condenser and vacuum outlet was charged with 50 g of Viscosil 10M (Mn=42,000 trimethylsilyl stopped polydimethylsiloxane, viscosity 10,000 cSt) and 0.75 g of decamethyltetrasiloxane as a chain stopper. The mixture was heated to 90° C., after reaching the desired temperature a 50 ppm (36 microliter of a 7% solution in methylene chloride) of $PCl_3(NPCl_2)_nNPCl_3 \cdot SbCl_6$ (n=1,2) was added. The reaction mixture was stirred at 90° C. A fast loss of viscosity was observed. After 30 minutes of reaction a low molecular weight polymer was formed; the viscosity of the reaction mixture went down to reach 600 cSt. The resulting trimethylsilyl stopped polydimethylsiloxane, viscosity 520 cSt has a molecular weight of Mn=1.5,600, a distribution, Mn/Mw=2.0 and contained less than 1.5% oligomeric cyclic species.

Figure 1:
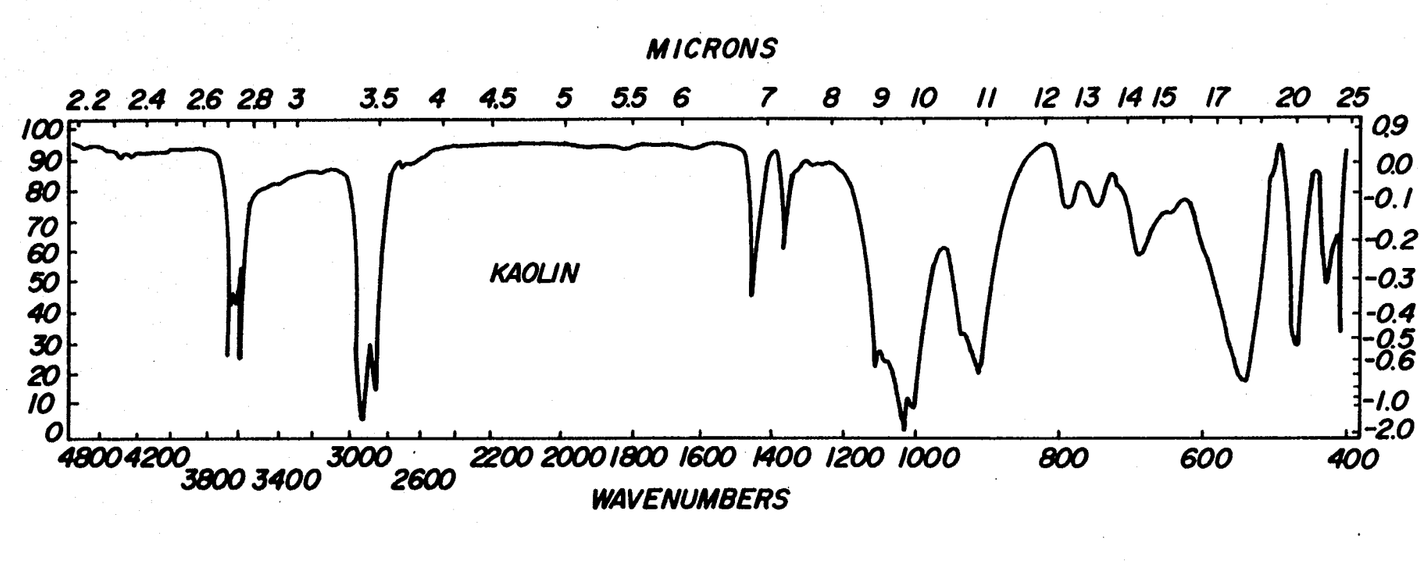
The drawing is a graphical representation of the infrared spectrum of a kaolin (aluminum silicate hydroxide) found to be a useful catalyst for disproportionation in accordance with the present invention.

The following three examples describe the disproportionation of siloxanes using kaolin as the catalyst. (See Drawing for analytical curve).

EXAMPLE 10

A three necked round-bottomed flask equipped with condenser and mechanical stirrer was charged with a 58.84 g of a 10,000 cps trimethylsiloxy-stopped silicone oil and 0.67 g hexamethyldisiloxane (1% by wt). The mixture ( 9450 cps; 1.8 % volatiles) was heated to 90° C. with stirring, then treated with 0.41 g of kaolin clay (Aldrich, 0.6 % by wt). After 30 minutes an aliqout was taken from the reaction mixture and filtered to remove kaolin. The siloxane filtrate measured 1086 cps with 2.4 % volatiles. A second aliquot taken after 60 minutes measured 590 cps with 3.5 % volatiles.

EXAMPLE 11

A three necked round-bottomed flask equipped with mechanical stirrer and condenser was charged with 48.2 g of a 10,000 cps trimethylsiloxy-stopped silicone oil and 1.59 g of decamethyltetrasiloxane (3.2 % by wt). The mixture (8600 cps, 4.6 % volatiles) was heated to 90° C. with stirring, then treated with 1.02 g of kaolin (Aldrich, 2% by wt). After 15 minutes all aliquot was taken from the reaction mixture and filtered to remove kaolin. The siloxane filtrate measured 353 cps with 4.8 % volatiles content.

EXAMPLE 12

This example measures the effect of silanols on disproportionations with kaolin.

A three necked round-bottom flask equipped with mechanical stirrer and condenser was charged with 66.84 g of a 3000 cps silanol-stopped silicone oil (about 1000 ppm SiOH content) and 2.21 g decamethyltetrasiloxane (3.2 % by wt). The mixture (2800 cps; 4.2 % volatiles) was heated to 90° C. with stirring, then treated with 1.36 g of kaolin (Aldrich; 2% by wt). After fifteen minutes an aliquot was removed from the reaction mixture and filtered to remove kaolin. The siloxane filtrate measured 1680 cps with 3.7 % volatiles. A second aliquot taken after 30 minutes and measured 1270 cps with 3.8 % volatiles

EXAMPLE 13

Synthesis of Vinyldimethyl-terminated Siloxane Oil by Disproportionation in the Presence of Trifluoromethanesulfonic Acid as Catalyst A 250 ml flask equipped with mechanical stirrer, condenser and vacuum outlet was charged with 50 g of polydimethylsiloxanediol (PS 341, MW=4,000, Hüls) and 5 g of vinyldimethylterminated siloxane oil (MW=3,200) as a chain stopper. The mixture was heated to 90° C. After reaching the specified temperature a 40 ppm (2 microliters) of trifluoromethanesulfonic acid was added. The reaction mixture was stirred under vacuum (0.1 mm Hg). A very fast polycondensation was observed (considerable foam was formed and water was condensed in vacuum trap). After a few minutes of reaction a high molecular weight polymer was formed (viscosity >200,000 cSt). In next 60 minutes the viscosity of reaction mixture went down to 2,800 cSt after 80 minutes. Addition of extra 40 ppm (2 microliters) of catalyst did not change viscosity of the resulting polymer. The resulting vinyldimethylterminated silicone oil has a MW=58,000 and contains less than 1 % oligomeric cyclic species.

EXAMPLE 14

Synthesis of Trimethylsilyl-terminated Siloxane Oil by Disproportionation in the Presence of Sulfuric Acid as Catalyst One hundred and fifty grams of a 10,000 cps trimethylsilyl endstopped polydimethylsiloxane was blended with 50 g of a 50 cps trimethylsilyl endstopped polydimethylsiloxane. The volatiles content of the blend was 0.2 wt%. The blend was heated to 90° C. and 50 ppm of 86% sulfuric acid was added. The viscosity, total volatiles content and cyclics content were followed with time. Volatiles were measured by weight loss at 135° C. and 15 torr for 45 minutes and the cyclics content was measured by gas chromatography with the following results:

| Time (min) | Viscosity (cps) | Total Volatiles, % | Cyclic Volatiles, % |
|---|---|---|---|
| 0 | 5603 | 0.2 | — |
| 10 | 4915 | 1.48 | — |
| 25 | 1087 | 1.75 | — |
| 50 | 617 | 2.19 | — |
| 80 | 357 | 2.71 | — |
| 200 | 270 | 6.00 | 3.0 |
| 310 | 225 | 6.20 | 3.1 |

In a second procedure, 200 g of a 10,000 cps trimethylsilyl endstopped polydimethyl siloxane were blended with 3.0 g of hexamethyldisiloxane and heated to 90° C. Five hundred ppm of 86% sulfuric acid was added and the viscosity, volatiles, and cyclics content were measured over time with the following results:

| Time (min) | Viscosity (cps) | Total Volatiles, % | Cyclic Volatiles, % |
|---|---|---|---|
| 10 | 718 | 3.7 | — |
| 30 | 304 | 4.9 | — |
| 40 | 191 | 5.5 | — |
| 50 | 172 | 6.0 | — |
| 70 | 130 | 6.4 | — |
| 80 | 142 | 6.6 | 3.5 |

Since the product is a low viscosity oil, the data in this example show that the disproportionation reaction will produce low molecular weight linear from the normal molecular weight distribution, and some of these linears are volatile under the volatiles test conditions. This example further shows that under these conditions, sulfuric acid will disproportionate to an average composition without the formation of significant cyclics. Sulfuric acid is a well known equilibration catalyst at higher temperatures and, at temperatures above 130° C., sulfuric acid is a classical equilibration catalyst which means that it will rearrange the above siloxane blends to form a low viscosity of normal molecular weight distribution, but such equilibration will also form 13–15% cyclics, further differentiating the present invention from the prior art.

EXAMPLE 15

Synthesis of Vinyldimethylterminated Siloxane Oil in the Presence of Short Chain Phosphazenes (a) Preparation of Catalyst Comprising Reaction Product of Linear Phosphonitrilic Chlorides and Acetic Acid (i) Preparation of Linear Phosphonitrilic Chlorides A 100 ml flask was charged with 20.5 g (0.5 mol) of phosphorus pentachloride, 2.7 g (0.05 mol) of ammonium chloride and 50 g of tetrachloroethane. The mixture was stirred and refluxed for 8 hours. After the reaction was over, the reaction mixture was poured into petroleum ether. The precipitate was dissolved in methylene chloride and reprecipitated with petroleum ether. After removing traces of solvent under vacuum, 14 g of light yellow crystals of the title product (PNC) were obtained.

(ii) Preparation of Catalytic Composition

A 50 ml flask was charged with 1 g (0.00154 mol) of PNC from Step (i) and 20 ml of methylene chloride. Then 0.185 g (0.00308 mol) of acetic acid was added at once at room temperature. The resulting mixture was stirred over 2 hours. During that time, evolution of HCl was observed. After 2 hours the solvent and low boiling material were removed from the system by heating to 80° C. under reduced pressure (0.05 mm Hg) for 2 hours to afford 0.7 g of light yellow viscous oil, which was dissolved in 14 ml of methylene chloride. This solution was used as a catalytic composition in following example.
(iii)

A 250 ml flask equipped with mechanical stirrer, condenser and vacuum outlet was charged with 50 g of polydimethylsiloxanediol (PS 341, MW=4,000, Hüls) and 5 g of vinyldimethylterminated siloxane oil (MW=4,200) as a chain stopper. The mixture was heated to 90° C. After reaching the desired temperature, 20 ppm (22 microliters of a 5% solution in methylene chloride) of the acetic acid modified catalyst (from step (ii)) was added. The reaction mixture was stirred under a vacuum of 0.1 mm Hg. Very fast polycondensation was observed (considerable foam was formed and water was condensed in vacuum trap). After 2 minutes of reaction a high molecular weight polymer was formed (viscosity>200,000 cSt). In the next 8 minutes the viscosity of the reaction mixture went down to reach 2,600 cSt after 10 minutes. Addition of an extra 20 ppm of catalyst at this point did not change the viscosity of the resulting polymer. The resulting vinyldimethyl-terminated silicone oil has MW=50,000 and contains less than 1% of oligomeric cyclic species.

EXAMPLE 16

Synthesis of Low Molecular Weight Vinyldimethyl-terminated Siloxane Oil in the Presence of Short-chain phosphazenes A 250 ml flask equipped with mechanical stirrer, condenser and vacuum outlet was charged with 50 g of vinyldimethyl-terminated siloxane oil (MW=50,000) from Example 21 and 4.25 g of divinyltetramethyldisiloxane as a chain stopper. The mixture was heated to 90° C., after reaching desired temperature a 20 ppm (22 microliters of a 5% solution in methylene chloride) of catalyst (from Example 15, step (ii)) was added. The reaction mixture was stirred at 90° C. A fast loss of viscosity was observed. After 20 minutes of reaction the viscosity of the polymer went down to 31 cSt. Addition of an extra 20 ppm of catalyst at this point did not change viscosity of resulting polymer. The resulting vinyldimethyl-terminated silicone oil has MW=4,200 and contains a small amount of oligomeric cyclic species.

EXAMPLE 17

Synthesis of Vinyldimethyl-terminated Siloxane Oil in the Presence of Short-chain phosphazenes A 250 ml flask equipped with mechanical stirrer, condenser and vacuum outlet was charged with 50 g of polydimethylsiloxanediol (PS 341, MW=4,000, Hüls) and 3 g of vinyldimethyl-terminated siloxane oil (MW=4,200) as a chain stopper. The mixture was heated to 90° C. After reaching the specified temperature a 20 ppm (12 microliters of 9% solution in ethyl acetate) of catalyst (from Preparation A above) was added. The reaction mixture was stirred under a vacuum of 0.1 mm Hg. A very fast polycondensation was observed (considerable foam was formed and water was condensed in the vacuum trap). After a few minutes of reaction a high molecular weight polymer was formed (viscosity>100,000 cSt) In 20 minutes, the viscosity went down to reach 40,000 cSt). At this point an extra 12 microliters of catalyst was added. In the next 2 hours, the viscosity of the reaction mixture went down to reach finally 18,000 cSt.

EXAMPLE 18

Synthesis of Vinyldimethyl-terminated Siloxane Oil in the Presence of Short-chain Phosphazenes

A 250 ml flask equipped with mechanical stirrer, condenser and vacuum outlet was charged with 50 g of polydimethylsiloxanediol (PS 341, MW=4,000, Hüls) and 3 g of vinyldimethylterminated siloxane oil (MW=4,200) as a chain stopper. The mixture was heated to 90° C. After reaching the specified temperature, 28 ppm (17 microliters of 9% solution in ethyl acetate) of catalyst (from Procedure B above) was added. The reaction mixture was stirred under vacuum of 0.1 mm Hg. A very fast polycondensation was observed (considerable foam was formed and water was condensed in the vacuum trap). After a few minutes of reaction a high molecular weight polymer was formed (viscosity>100,000 cSt). In 10 minutes the viscosity went down to 23,000 cSt. After an additional 50 minutes the viscosity of the polymer reached 17,200 cSt. At this point an extra 17 microliters of catalyst was added. In the next 2 hours the viscosity of reaction mixture went down to reach a final viscosity of 15,500 cSt.

The above-mentioned patents, publications and Test Methods are incorporated herein by reference.

Many variations of the invention will suggest themselves to those skilled in this art in light of the above, detailed description. All such obvious modifications are within the full intended scope of the appended claims.

We claim:

1. A process for producing an organosiloxane of the formula:

Formula I wherein $R^1$ is selected from the group consisting of saturated hydrocarbons having from 1 to 8 carbon atoms, unsaturated hydrocarbons having from 2 to 8 carbon atoms, aryl hydrocarbons having from 6 to 8 carbon atoms and halogenated hydrocarbons having from 1 to 8 carbon atoms; $R^2$ is $R^1$ or $R^1$-O; $R^3$ is selected from the group consisting of $R^1$, hydrogen and OH; n is 1 to 5000;

and the ratio of the sum of $R^1+R^2+R^3$ to silicon atoms in the final product is from 1.9 to 2.1, said process comprising disproportionating a mixture of a siloxane of the formula:

Formula II wherein $R^1$, $R^2$ and $R^3$ are the same as herein above defined and r has a value of 500 to 15,000; and a siloxane of the formula:

Formula I wherein $R^1$ is selected from the group consisting of saturated hydrocarbons having from 1 to 8 carbon atoms, unsaturated hydrocarbons having from 1 to 8 carbon atoms, aryl hydrocarbons having from 6 to 8 carbon atoms and halogenated hydrocarbons having 1 to 8 carbon atoms; $R^2$ is $R^1$ or $R^1$-O; $R^3$ is selected from a group consisting of $R^1$, hydrogen and OH; n is 1 to 5000; and the ratio of the sum of $R^1+R^2+R^3$ to silicon atoms in the final product is from 1.9 to 2.1, said process comprising, as a first step

(I) providing a starting material of Formula IIa

Formula IIa wherein $R^1$, $R^2$ and $R^3$ are the same as herein above defined and r' has a value of 500 to 15,000 by condensing a corresponding disilanol terminated organosiloxane having a Si—OH content above 1000 ppm wherein r has a value of from 10 to 15,000 by means of a condensation catalyst until the Si—OH content is reduced to below about 1000 ppm, and, thereafter, as a second step, (II) disproportionating a mixture of the condensed siloxane produced in step (I) of the formula:

Formula II wherein $R^1$, $R^2$ and $R^3$ are the same as herein above defined and r has a value of 500 to 15,000; and a siloxane of the formula:

Formula III wherein $R^1$, $R^2$ and $R^3$ are the same as herein above defined and s has a value of 0 to 300, with the proviso that the total amount of silanol in Formula I and II may not exceed about 1000 ppm by weight; in the presence of an effective disproportionating amount of a catalyst which comprises a compound which is capable of disproportionating said mixture of an organosiloxane of Formula II and Formula III without substantially increasing the cyclics content of said mixture; and thereafter recovering an organosiloxane of Formula I.

13. A process as defined in claim 1 wherein the disproportionation reaction is terminated by increasing the temperature to a temperature of from 150° to 250° C.

14. A process as defined in claim 1 wherein the dispoportionation reaction is terminated by the addition of a neutralizing agent.

15. A process as defined in claim 1 wherein the compound of Formula III is hexamethyldisiloxane.

16. A process as defined in claim 10 wherein the compound of Formula III is symtetramethyldivinyldisiloxane.

* * * * *

Formula III wherein $R^1$, $R^2$ and $R^3$ are the same as herein above defined and s has a value of 0 to 300, with the proviso that the total amount of silanol in Formula I and II may not exceed about 750 ppm by weight; in the presence of an effective disproportionating amount of a catalyst which comprises a compound which is capable of disproportionating said mixture of an organosiloxane of Formula II and Formula III without substantially increasing the cyclics content of said mixture; and thereafter recovering an organosiloxane of Formula I.

2. A process as defined in claim 1 wherein said catalyst compound has the ability to effect the conversion of a mixture of polyorganosiloxane of Formula II and the polyorganosiloxane of Formula III to a disproportionated product of Formula I, at a temperature of about 90° C., within a relatively short time, in the range of from about 30 to about 90 minutes, without, at the same time, substantially increasing the content of cyclic by-products.

3. A process as defined in claim 1 wherein said catalytic compound is selected from a phosphorus-nitrogen homopolymeric compounds, a derivative thereof, sulfuric acid, a fluorinated alkane sulfonic acid, a kaolin clay, or a mixture of any of the foregoing.

4. A process as defined in claim 1 wherein the catalyst is of the formula: $Cl_3PN(PNCl_2)_xPCl_3 \cdot PCl_6$ (x=0,1 or 2).

5. A process as defined in claim 1 wherein the catalyst is of the general Formulae (Ia) or (Ib):

$$O(X)_{2-m}Y_mP\{NP(X)_2\}_nNP(X)_{3-q}(Y)_q \qquad (Ia)$$

$$O(X)_{2-m}Y_mP\{NP(X)_2\}_nN(H)P(O)(X)_{2-p}(Y)_p \qquad (Ib)$$

where n=O or an integer from 1 to 8; m=0 or an integer of 1; p=0 or an integer of 1; q=0 or an integer of from 1 to 2; X=halogen; Y=OH, OR, O(O)CR, wherein R is alkyl or aryl.

6. A process as defined in claim 1 wherein the catalyst is of the Formulae (Ic), (Id) or (Ie):

$$OCl_2P(NPCl_2)_nNPCl_2OH, \qquad (Ic)$$

$$OCl_2P(NPCl_2)_nN(H)PCl_2O, \qquad (Id)$$

$$OCl_2P(NPCl_2)_nNPCl_3, \qquad (Ie)$$

where n is 0 or an integer of from 1 to 8.

7. A process as defined in claim 1 wherein the catalyst is of the formula: $Cl_3P(NPCl_2)_xNPCl_3 \cdot SbCl_6$ (x=2).

8. A process as defined in claim 1 wherein the catalyst is the reaction product of a linear phosphonitrilic chloride and acetic acid.

9. A process as defined in claim 1 wherein the catalyst is trifluoromethanesulfonic acid.

10. A process as defined in claim 1 wherein the catalyst is a kaolin clay.

11. A process as defined in claim 1 wherein n is an integer of from 5 to 1000.

12. A two-step process for producing an organosiloxane of the formula: